United States Patent [19]

Nagase et al.

[11] Patent Number: 4,564,639
[45] Date of Patent: Jan. 14, 1986

[54] N-(2,6-DIFLUOROBENZOYL-N-′-(2-FLUORO-4-HALOPHENYL)UREA

[75] Inventors: Hiroshi Nagase, Kawanishi; Yasuo Sato, Kyoto, both of Japan

[73] Assignee: Takeda Chemical Industries, Ltd., Osaka, Japan

[21] Appl. No.: 471,191

[22] Filed: Mar. 1, 1983

[30] Foreign Application Priority Data

Mar. 1, 1982 [JP]  Japan ................................. 57-32623
Dec. 9, 1982 [JP]  Japan ............................... 57-215835

[51] Int. Cl.⁴ ..................... C07C 127/22; A01N 47/28
[52] U.S. Cl. ........................................ 514/594; 564/44
[58] Field of Search .................... 424/322; 564/44; 514/594

[56] References Cited

U.S. PATENT DOCUMENTS

| | | | |
|---|---|---|---|
| 3,933,908 | 6/1976 | Wellinger et al. | 564/44 |
| 3,989,842 | 11/1976 | Wellinger et al. | 424/322 |
| 4,085,226 | 4/1978 | Sirrenberg et al. | 424/322 |
| 4,243,680 | 1/1981 | Taylor | 424/322 |
| 4,276,310 | 6/1981 | Sirrenberg et al. | 564/44 X |

FOREIGN PATENT DOCUMENTS

EP52833  6/1982  European Pat. Off. ............. 564/44
EP88343  9/1983  European Pat. Off. ............. 564/44

*Primary Examiner*—Thomas A. Waltz
*Attorney, Agent, or Firm*—Burgess, Ryan & Wayne

[57] ABSTRACT

A urea derivative of the general formula,

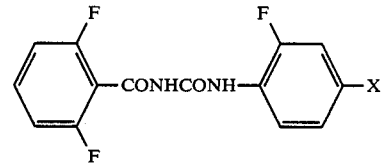

(wherein X is a halogen), which has higher insecticidal activity than known similar compounds, with lowered toxicity to mammals and fishes. The derivative can be produced by reacting 2-fluoro-4-haloaniline with 2,6-difluorobenzoyl isocyanate or reacting 2-fluoro-4-halo-phenylisocyanate with 2,6-difluorobenzamide.

18 Claims, No Drawings

N-(2,6-DIFLUOROBENZOYL-N-'-(2-FLUORO-4-HALOPHENYL)UREA

The present invention relates to novel urea derivatives of the general formula:

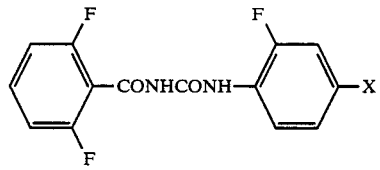
[I]

[wherein X is a halogen atom], which exhibit excellent insecticidal effect.

As the urea derivatives exhibiting insecticidal effect, hitherto, a variety of N-(2,6-dihalogenobenzoyl)-N'-(substituted phenyl)urea derivatives have been reported (the Japanese Patent Publication Nos. 18255/1977, 43952/1978 and 900/1979, the U.S. Pat. No. 3,748,356, the Japanese Unexamined Published Patent Application No. 31092/1980, etc.), but their insecticidal effects are far from being satisfactory. Out of these, the Japanese Patent Publication Nos. 18255/1975, 43952/1978 and 900/1979 (the latter two are concerned with the divisional applications of the former application for patent), and the U.S. Pat. No. 3,748,356 describe the compounds similar to the compounds [I] of the present invention, such as N-(2,6-difluorobenzoyl)-N'-(3-fluoro-4-chlorophenyl)urea and N-(2,6-difluorobenzoyl)-N'-(3-fluoro-4-iodophenyl)urea, but give no concrete description of the compounds [I] of the present invention, while some contain mention of urea derivatives having one or two substituents at the 3- or 4-position on the N'-substituted phenyl ring, which exhibit the maximal activity. The present inventors, in the course of extensive investigation on a great variety of urea derivatives and their insecticidal activity and action, succeeded in the synthesis of the compounds [I] having fluorine and a halogen at the 2- and 4-positions on the N'-substituted phenyl ring, respectively, and found that these unexpectedly possess insecticidal and ovicidal activities superior to those of known compounds of the analogous structures and also display lowered toxicity to mammals and fishes and exert lessened hazard on the environment. The finding was followed by further intensive research, which has culminated in the present invention.

Thus, the present invention relates to:

(1) A urea derivative of the general formula [I], (2) A process for producing a urea derivative of the general formula [I], characterized in that said process comprises reacting a compound of the general formula:

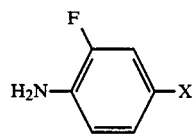
[II]

[wherein X is a halogen] with 2,6-difluorobenzoyl isocyanate, or reacting a compound of the general formula:

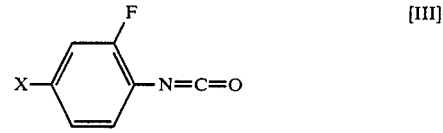
[III]

[wherein X is a halogen] with 2,6-difluorobenzamide, and (3) An insecticidal composition, characterized in that said composition contains a compound of the general formula [I].

In the above general formulae, as the halogen atom represented by X, use is for example made of fluorine, chlorine, bromine and iodine.

Particularly noticeable in the present invention are the highly potent insecticidal and ovicidal actions of the compounds [I], which can produce satisfactory effects at lowered application rates as compared with the known analogous compounds. In addition to possessing the economical advantage of rendering the application rate less, consequently, the compounds [I] display extremely lowered toxicity to mammals [the compounds of the general formula [I] where X is fluorine, chlorine, bromine and iodine, respectively, each show not less than 3 g/kg in $LD_{50}$ in mice (oral)], along with low toxicity to fishes (the compound of the general formula [I] where X is chlorine shows not less than 10 ppm/72 hours later in TLm (the concentration at which 50% of the test fish dies) in orange-red killifish (*Orizias latipes*)), thus exerting lessened hazard on the environment.

In particular, the compound of the general formula [I] where X is chlorine or bromine exhibits excellent insecticidal and ovicidal effect.

Also, the compounds [I] of the present invention, which not only excel in rapid acting property but also show the tendency to penetrate into the plant body due to absorption through plant roots, have the outstanding, characteristic feature that the known analogous compounds fail to present. Among others, the compound of the general formula [I] where X is fluorine possesses the excellent action to penetrate into the plant body.

In general, the known analogous compounds display insecticidal activity through oral intake into the insect body (The Japanese Patent Publication Nos. 18255/1977, 43952/1978 and 900/1979, and J. Agric. Food Chem., 21, 348 (1973)), but the compounds [I] of the present invention demonstrates highly insecticidal effect even when applied on the surface of the insect body.

Since the compounds [I] of the present invention show extremely low toxicity to mammals, furthermore, they can be safely utilized in cattle sheds, etc. for the extermination of ectoparasites of mammals.

The compounds [I] of the present invention are effective in the control of household and forestry insect pests, plant parasitic insects, etc.

In more particular, the compounds [I] of the present invention and preparations containing them are especially effective in the control of harmful insects of Hemiptera such as *Eurydema rugosa, Scotinophara lurida, Riptortus clavatus, Stephanitis nashi, Laodelphax stiatellus, Nephotettix cincticeps, Unaspis yanonensis, Aphis glycines, Lipaphis pseudobrassicae, Brevicoryne brassicae* and *Aphis gossypii*, harmful insects of Lepidoptera such as *Spodoptera litura, Plutella xylostella, Pieris rape crucivora, Chilo suppressalis, Plusia nigrisigna, Helico-*

*vorpa assulta, Leucanla separata, Mamestra brassicae, Adoxophyes orana, Syllepta derogata, Cnaphaloerocis medinalis, Phthorimaea operculella, Hyphautria cunea* and *Lymantria dispar*, harmful insects of Coleoptera such as *Epillachna vigintioctopunotata, Aulacophora femoralis, Phyllotreta striolata, Oulema orgzae, Echinocnemus squameus, Leptinotorsa decemlineata, Lissorphopterus oryzophilus* and *Anthononus grandis*, harmful insects of Diptera such as *Musca domestica, Culex pipiens pallens, Tabonus trigonus, Hylemya antigua* and *Hylemyn platura*, harmful insects of Orthoptera such as *Locusta migratoria* and *Gryllotalpa africana*, harmful insects of Blattidae such as *Blattella germanica* and *Periplaneta fuliginosa*, harmful insects of Isoptera such as *Ceucotermes speratus*, nematodes such as *Aphelenchoides besseyi*, and others.

In using the compounds [I] of the present invention as insecticide, they are employed in the forms which general agricultural chemicals can assume, namely in the preparation forms such as emulsifiable concentrates, oil-borne preparations, wettable powders, dusts, granules, preparations for spraying uses and ointments prepared by dissolving or suspending in a suitable liquid carrier, or mixing or adsorbing with an appropriate solid carrier, one or two kinds of the compounds [I], according to the intended application purpose. Among these, preferred preparation forms include emulsifiable concentrates, wettable powders, dusts, granules, etc. These preparations may be supplemented with emulsifiers, suspending agents, spreaders, penetrants, wetting agents, thickening agents, stabilizers, etc., if necessary, and can be prepared by a procedure known per se.

The proportion in which the active ingredient is contained in the insecticide according to the present invention varies depending upon the application purpose, and is suitably in the range of 10 to 90 weight % for emulsifiable concentrates, wettable powders, etc., appropriately in the region of 0.1 to 10 weight % for oil-borne preparations, dusts, etc., and properly in the range of 1 to 20 weight % for granules, although such concentrations may be conveniently changed with the intended application purpose. Further, emulsifiable concentrates, wettable powders, etc. may be sprayed after diluting and extending suitably with water, etc. (for example, to 100 to 100,000 times) on the occasion of application.

Suitable examples of the liquid carrier which is useful include water, alcohols (e.g., methyl alcohol, ethyl alcohol, ethylene glycol, etc.), ketones (e.g., acetone, methyl ethyl ketone, etc.), ethers (e.g., dioxane, tetrahydrofuran, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.), halogenated hydrocarbons (e.g., chloroform, carbon tetrachloride, etc.), acid amides (e.g., dimethylformamide, dimethylacetamide, etc.), esters (e.g., ethyl acetate, butyl acetate, mono- di- or tri-glycerine esters of lower (having 2 to 6 carbon atoms) fatty acids, etc.), nitriles (e.g., acetonitrile, etc), and other solvents, and one kind of these or mixtures of not less than two kinds of these are utilized. As the solid carrier, use is made of vegetable powders (e.g., soybean meal, tobacco meal, wheat flour, wood flour, etc.), mineral powders (e.g., clays such as kaolin, bentonite and acid clay, talc such as talc powder and azalmatolite powder, silicas such as diatomaceous earth and mica powder, etc.), alumina, sulfur powder, activated carbon and the like, and one of, or mixtures of not less than tow kinds of, these are utilized.

As the ointment base, suitably selected can be one or not less than two kinds of for example polyethylene glycol [$H(OCH_2CH_2)_nOH$ where n is about 4 to 14], pectin, polyhydric alcohol esters of higher (having 10 to 20 carbon atoms) fatty acids such as mono-, di- or tri-glycerine esters of stearic acid, cellulose derivatives such as methylcellulose, sodium arginate, bentonite, higher alcohols, polyhydric alcohols such as glycerine, petrolatum, white petrolatum, liquid paraffin, lard, various kinds of vegetable oils, lanolin, lanolin anhydricum, hardened oil, resins, etc., either solely or added with various surfactants and others.

As the surfactants which are used as emulsifiers, spreaders, penetrants, dispersing agents, etc., use is made of soaps, polyoxyalkyl aryl esters (e.g., Nonal ®) produced by Takemoto Oils & Fats Co., Japan), alkyl sulfates (e.g., Emal 10 ® and Emal 40 ® produced by Kao Atlas Co., Japan), alkyl sulfonates (e.g., Neogen ®, Neogen T ®, etc. produced by Dai-ichi Kogyo Seiyaku Co., Japan); Neopelex ®, produced by Kao Atlas Co., Japan), polyethylene glycols (e.g., Nonipol 85 ®, Nonipol 100 ®, Nonipol 160 ®, etc. produced by Sanyo Chemical Industries, Japan), polyhydric alcohol esters (e.g., Tween 20 ®, Tween 80 ®, etc. produced by Kao Atlas Co., Japan), etc., if necessary. Also, the compounds [I] can be used as mixtures by formulating simultaneously for example other kinds of insecticides (e.g., pyrethrin type insecticides, organic phosphate type of insecticides, carbamate type of insecticides, natural or botanical insecticides, etc.), acaricides, nematocides, herbicides, plant hormones, plant growth regulators, fungicides (e.g., copper based fungicides, chlorinated hydrocarbon type of fungicides, organic-sulfur based fungicides, phenol-based fungicides, etc.), synergists, attractants, repellants, coloring matters, fertilizers, etc.

In utilizing the compounds [I] of the present invention, their desired application amount varies with various factors such as the scope of application and type of preparation forms, and is normally about 10 to about 2000 g/ha. Needless to say, the application amount may be conveniently increased or decreased.

The compounds [I] of the present invention can be produced for example by reacting an aniline derivative of the general formula [II] with 2,6-difluorobenzoyl isocyanate. In this reaction, 2,6-difluorobenzoyl isocyanate is used in the range of 1 to 1.2 moles per mole of the compound [II]. The reaction is desirably carried out normally in a suitable solvent, for example in inert solvent such as aromatic hydrocarbons exemplified by benzene, toluene and xylene, halogenated hydrocarbons exemplified by dichloromethane, chloroform and carbon tetrachloride, ethers exemplified by ethyl ether, dioxane and tetrahydrofuran, nitriles exemplified by acetonitrile, esters exemplified by ethyl acetate, and hydrocarbons exemplidied by petroleum ether, petroleum benzine and hexane. The reaction temperature is normally about 0° to about 120° C., preferably about 10° C. to about 50° C. The reaction proceeds within a period in the range of 5 minutes to 24 hours, and normally goes to conclusion within a period in the range of 20 minutes to 2 hours. The conclusion of the reaction can be recognized by means of thin-layer chromatography and the like.

Furthermore, the compounds [I] of the present invention can be produced by reacting a compound [III] with 2,6-difluorobenzamide.

The compound [III] may be used in the range of 1 to 1.2 moles per mole of 2,6-difluorobenzamide.

The reaction is preferably carried out normally in a solvent, whereby use is made of inert solvents such as aromatic hydrocarbons exemplified by benzene, toluene and xylene, hydrocarbons exemplified by hexane and petroleum benzin, and halogenated hydrocarbons exemplified by dichloroethane and carbon tetrachloride. The reaction temperature can be conveniently selected from the range of about 30° to about 150° C., and is desirably about 50° to about 150° C. The reaction goes to conclusion within a period in the range of 1 to 24 hours. The conclusion of the reaction can be recognized by means of thin-layer chromatography and the like. The compounds [I] of the present invention can be isolated and purified from the reaction mixture by the per se known means such as crystallization, recrystallization, precipitation, extraction, concentration and chromatography.

The compounds [II] and [III], 2,6-difluorobenzoyl isocyanate and 2,6-difluorobenzamide, which are useful as the starting material for the production of the compounds [I] of the present invention, can be produced by the already known procedures or procedures similar thereto.

The compounds [II] can be produced by the procedures as described for example in the Japanese Unexamined Published Patent Application No. 23962/1978, the U.S. Pat. No. 3,990,880 and J. Chem. Soc. (C), 1970, 2106, etc.; the compounds [III] can be prepared by the methods as mentioned for example in J. Agr. Food Chem., 21, 348 (1973) and Fieser and Fieser, Reagents for Organic Synthesis, pp. 842, published by John Wiley and Sons, Inc. (1967); 2,6-difluorobenzoyl isocyanate can be prepared by the procedure as described for example in J. Org. Chem., 27, 3742 (1962), and 2,6-difluorobenzamide can be prepared by the method as mentioned for example in J. Med. Chem., 11, 814 (1963). Also, the starting compounds [III] can be produced for example by reacting the compound [II] with phosgen. In the reaction, phosgene can be used in the proportion in the range of 1 to 5 moles per mole of the compound [III], preferably in the range of 2 to 4 moles.

This reaction is normally carried out in suitable solvent, use is made of inert solvents such as aromatic hydrocarbons exemplified by benzene, toluene and xylene, and hydrocarbons exemplified by petroleum benzin and hexane. The reaction temperature ranges from about 50° to about 150° C., preferably from about 70° to about 130° C. The reaction time varies with the reaction time, as well, and is normally in the region of 30 minutes to 5 hours.

The compounds [III] thus obtained are a liquid at normal temperature under atmospheric pressure, and can be isolated and purified by the known means such as concentration, extraction, distillation, distillation under reduced pressure and chromatography.

The Reference Examples, Examples and Test Examples are more specifically described in the following, but the present invention is not intended to be limited by these Examples.

REFERENCE EXAMPLE 1

2-Fluoro-4-chlorophenyl isocyanate

A 600 g quantity of phosgene was absorbed in 1.4 l of toluene at 5° to 6° C., and then, a solution of 220 g of 2-fluoro-4-chloroaniline in 700 ml of toluene was gradually added to the solution. Thereafter, the reaction solution was warmed slowly and stirred under heating at about 110° C. for 3 hours. After the conclusion of the reaction, the reaction mixture was concentrated under reduced pressure and distilled under reduced pressure to give 184 g of the subject 2-fluoro-4-chlorophenyl isocyanate, boiling point: 84°-85° C./15 mmHg.

REFERENCE EXAMPLE 2

By the same procedure as in Reference Example 1, there was obtained 2-fluoro-4-bromophenyl isocyanate as an oily substance of boiling point of 53°-57° C./2 mmHg.

REFERENCE EXAMPLE 3

2,6-Difluorobenzoyl isocyanate

In 150 ml of dichloroethane was suspended 13.5 g of 2,6-difluorobenzamide, and 14.0 g of oxalyl chloride was little by little added to the suspension, followed by heating under reflux at about 110° C. for 15 hours. The reaction mixture was concentrated under reduced pressure, and the resultant oily substance was distilled under reduced pressure to give 12 g of the subject compound as an oily material of boiling point of 123° C./60 mmHg.

EXAMPLE 1

N-2,6-Difluorobenzoyl-N'-2-fluoro-4-chlorophenylurea (Compound No. 1)

In 50 ml of toluene was dissolved 1.6 g of 2-fluoro-4-chloroaniline, and 2.0 g of 2,6-difluorobenzoyl isocyanate was added dropwise to the solution under stirring at room temperature. After stirring was effected for 30 minutes, 50 ml of n-hexane was added, and an insoluble matter was recovered by filtration and washed with a small amount of n-hexane to give 3.2 g of crude crystals (melting point: 194°-196° C.). Recrystallization of such crystals from acetone yielded 2.6 g of colorless, needle-like crystals of the subject compound, melting point: 198°-199° C.

Elemental analysis for $C_{14}H_8N_2O_2F_3Cl$: Calcd.(%): C, 51.16; H, 2.45; N, 8.52. Found (%): C, 51.07; H, 2.40; N, 8.41.

IR (nujol) $\nu_{max}{}^{cm-1}$: 3220, 3120, 1720, 1700.

EXAMPLE 2

N-2,6-difluorobenzoyl-N'-2-fluoro-4-bromophenylurea (Compound No. 2)

In 50 ml of toluene was dissolved 2.1 g of 2-fluoro-4-bromoaniline, and 2.0 g of 2,6-difluorobenzoyl isocyanate was added dropwise to the solution under stirring at room temperature. After stirring was effected for 30 minutes, 50 ml of n-hexane was added, and an insoluble matter was recovered by filtration and washed with a small amount of n-hexane to give 3.7 g of crude crystals (melting point: 190°-192° C.). Recrystallization of such crystals from acetone yielded 3.0 g of colorless needle-like crystals of the subject compound, melting point: 195°-196° C.

Elemental analysis for $C_{14}H_8N_2O_2F_3Br$: Calcd. (%): C, 45.07; H, 2.16; N, 7.51. Found (%): C, 45.07; H, 2.11; N, 7.44.

IR (nujol) $\nu_{max}{}^{cm-1}$: 3230, 3120, 1715, 1695.

EXAMPLE 3

N-2,6-difluorobenzoyl-N'-2-fluoro-4-chlorophenylurea
(Compound No. 1)

A mixture consisting of 2.0 g of 2,6-difluorobenzamide, 2.2 g of 2-fluoro-4-chlorophenyl isocyanate and 100 ml of xylene was heated under reflux for 20 hours. After the conclusion of the reaction, the reaction solution was cooled, and the crystals which separated out were recovered by filtration and further recrystallized from acetone. Yield 3.0 g; melting point 198°–199° C. When the resultant compound was subjected to mixed melting with the sample as obtained in Example 1, there was no depression was observed in melting point.

EXAMPLE 4

N-2,6-difluorobenzoyl-N'-2,4-difluorophenyl urea
(Compound No. 3)

In 50 ml of toluene was dissolved 1.3 g of 2,4-difluoroaniline, and 1.8 g of 2,6-difluorobenzoyl isocyanate was added dropwise to the solution under stirring at room temperature. After stirring was effected for 30 minutes, precipitates were recovered by filtration and washed with a small amount of toluene to give 3.1 g of crude crystals. Recrystallization from acetone yielded 2.0 g of colorless crystals of the subject compound, melting point: 178°–179° C.

Elemental analysis, for $C_{14}H_8N_2O_2F_4$: Calcd. (%): C, 53.86; H, 2.58; N, 8.97. Found (%): C, 53.90; H, 2.54; N, 8.99.

IR (nujol) $\nu_{max}^{cm-1}$: 3220, 3120, 1720, 1700.

EXAMPLE 5

N-2,6-difluorobenzoyl-N'-2,4-difluorophenylurea
(Compound No. 3)

A mixture consisting of 2.0 g of 2,6-difluorobenzamide, 2.2 g of 2,4-difluorophenyl isocyanate and 100 ml of xylene was heated under reflux for 2.5 hours. After the conclusion of the reaction, the reaction mixture was cooled, and the crystals which separated out were recovered by filtration and recrystallized from acetone. Yield 2.0 g; melting point 178°–179° C. When the crystals so obtained were subjected to mixed melting with the sample as obtained previously in Example 4, there was no depression in melting point, and comparison of both samples gave good agreement for IR spectrum.

EXAMPLE 6

N-2,6-difluorobenzoyl-N'-2-fluoro-4-iodophenylurea
(Compound No. 4)

In 30 ml of toluene was dissolved 2.0 g of 2,6-difluorobenzoyl isocyanate, and 2.6 g of 2-fluoro-4-iodoaniline was added to the solution under stirring at room temperature. After stirring was effected for 2 hours, a precipitate was recovered by filtration and washed with a small amount of toluene to give 4.3 g of crystals of the subject compound, melting point; 209°–210° C.

Elemental analysis, for $C_{14}H_8N_2O_2F_3I$: Calcd. (%): C, 40.02; H, 1.92; N, 6.67. Found (%): C, 40.10; H, 1.87; N, 6.74. IR (nujol) $\nu_{max}^{cm-1}$: 3230, 3120, 1715, 1695.

EXAMPLE 7

Emulsifiable Concentrate

Compound No. 1: 20 weight %
Dimethylformamide: 75 weight %
Polyoxyethylene glycol ether (Nonipol 85®, produced by Sanyo Chemical Industries, Japan): 5 weight %

An emusifiable concentrate (which, on the occasion of application, is to be diluted with water to a given concentration and to be sprayed) prepared by mixing the above ingredients.

EXAMPLE 8

Wettable Powder

Compound No. 40: 25 weight %
Polyoxyethylene glycol ether (Nonipol 85®, produced by Sanyo Chemical Industries, Japan): 6 weight %
Diatomaceous earth: 69 weight %

A wettable powder (which, on the occasion of application, is to be diluted with water to a given concentration and to be sprayed) prepared by mixing the above ingredients.

EXAMPLE 9

Wettable Powder

Compound No. 2: 25 weight %
Sodium lignin sulfate: 5 weight %
Polyoxyethylene glycol ether (Nonipol 85®, produced by Sanyo Chemical Industries, Japan): 5 weight %
Clay: 65 weight %

A wettable powder (which, on the occasion of application, is to be diluted with water to a given concentration and to be sprayed) prepared by uniformly mixing and pulverizing the above ingredients.

EXAMPLE 10

Powder

Compound No. 2: 5 weight %
Clay: 95 weight %

A powder produced by uniformly mixing and pulverizing the above ingredients.

EXAMPLE 11

Powder

Compound No. 3: 10 weight %
Clay: 89.3 weight %
Silicone: 0.5 weight %
Polyethylene glycol ether: 0.2 weight %

A powder produced by uniformly mixing and pulverizing the above ingredients.

EXAMPLE 12

Granule

Compound No. 3: 5 weight %
Clay: 72 weight %
Bentonite: 20 weight %

The above ingredients were uniformly mixed and pulverized, and water of 8 weight % against the total weight was added, followed by kneading thoroughly. By following subsequently the conventional procedure, the mixture was processed into granules, which were dried to produce a granular preparation.

EXAMPLE 13

Granule

Compound No. 1: 2 weight %
Sodium lignin sulfonate: 5 weight %

Bentonite: 93 weight %

The above ingredients were uniformly mixed and pulverized, and water of 10 weight % against the total volume was added, followed by kneading. By following subsequently the conventional procedure, the mixture was processed into granules, which were dried to produce a granular preparation.

Test Example 1

Insecticidal effect against *Spodoptera litura*

(a) The test compounds which comprise:
The compounds [I] of the present invention;
wherein X is chlorine (Compound No. 1)
wherein X is bromine (Compound No. 2)
wherein X is fluorine (Compound No. 3)
wherein X is iodine (Compound No. 4).
As well as control compounds including;

(1) N-2,6-difluorobenzoyl-N'-4-chlorophenylurea (tradename: Dimilin, hereinafter referred to briefly as "Compound A"), (2) N-2,6-dichlorobenzoyl-N'-2,4-dichlorophenylurea (hereinafter referred to briefly as "Compound B"), (3) N-2,6-dichlorobenzoyl-N'-3-fluoro-4-chlorophenylurea (hereinafter referred to briefly as "Compound C"), (4) N-2,6-difluorobenzoyl-N'-3-fluoro-4-chlorophenylurea (hereinafter referred to briefly as "Compound D"), (5) N-2,6-difluorobenzoyl-N'-3,4-dichlorophenylurea (hereinafter referred to briefly as "Compound E"), (6) N-2,6-dichlorobenzoyl-N'-2,4-difluorophenylurea (hereinafter referred to briefly as "Compound F"), and (7) N-2,6-difluorobenzoyl-N'-3-fluoro-4-iodophenylurea (hereinafter referred to briefly as "Compound G").

The above test compounds and control compounds were each processed into wettable powders in accordance with the same formula as in Example 9, followed by dilution with water to prepare emulsions containing 0.4 and 2 ppm, respectively. A spreader, Dyne ® (produced by Takeda Chemical Industries, Japan), was added to the emulsions in the proportion of 0.03 volume % against the total volume, respectively, and 20 ml of each of the emulsions so obtained was sprayed by use of a spray gun (spraying pressure of 1 kg/cm$^2$) on seedlings (14 days after germination) of soybean grown in pots in a spray chamber. 2 hours after spraying, two true leaves were cut away and contained each in their respective ice-cream cup (diameter of 6 cm and depth of 4 cm), into which 10 third-instar larvae of *Spodoptera litura* was released. After the releasing of larvae, the cups were placed in a room (25° C.), and the number of larvae, and the 96 hours was checked. The test was repeated twice, and the test results as expressed in terms of mortality (%) are shown in Table 1 (1).

(b) By the same procedure as in Example 7, the test compounds comprising the compounds of the present invention, i.e. Compound Nos. 1, 2, 3 and 4, and control compounds, i.e. Compounds A through G, were each processed into emulsifiable concentrates, which were then diluted with water to produce the aqueous solutions (containing 0.03 % v/v of added spreader, Dyne ® (produced by Takeda Chemical Industries, Japan)) containing 10 and 50 ppm of the test compounds, respectively. 20 ml of each of the aqueous solutions was sprayed on 10 third-instar larvae of *Spodoptera litura* placed in a cage of wire netting. 30 minutes after the spraying, the larvae were taken out of the cage of wire netting and placed in an ice cream cup (diameter of 6 cm and depth of 4 cm) containing soybean leaves, and a number of dead larvae was checked in accordance with the same method as the examination method as stated under (a) except that the larvae were allowed to stand for 48 hours in place of 96 hours. The test was repeated twice, and the test results as expressed in terms of mortality (%) are shown in Table 1 (II).

(c) Using the compounds of the present invention, i.e. Compound Nos. 1, 2, 3 and 4, and control compounds, i.e. Compounds A through G, as the test compounds, granules containing 2 weight % of the test compounds were prepared by the same procedure as in Example 13, and 250 and 500 mg of each of the granules were admixed, for the purpose of treatment, into the soil around roots of soybean plants grown in pots (diameter of 9 cm), respectively. The pots so treated were placed in a glass room (28° C.), and 10 days after the treatment, two true leaves were cut away and contained each in ice cream cups (diameter of 6 cm and depth of 4 cm). 10 third-instar larvae of *Spodoptera litura* were released into each of the ice cream cups, and a number of dead larvae was checked in accordance with the same method as the examination method as stated under (a). The test was repeated twice, and the test results as expressed in terms of mortality (%) are shown in Table 1 (III).

The mortalities in Test Examples 1 through 3 were calculated by the formula as mentioned below:

$$\text{Mortality} = 100 - \frac{\text{(number of grown adults)}}{\text{(number of tested larvae)}} \times 100$$

TABLE 1

| | I Spraying concn. ppm | | II Spraying concn. ppm | | III Treatment amount mg | |
|---|---|---|---|---|---|---|
| Test compound | 0.4 | 2 | 10 | 50 | 250 | 500 |
| The compounds of the present invention: | | | | | | |
| Compound No. 1 | 100 | 100 | 60 | 100 | 90 | 100 |
| Compound No. 2 | 100 | 100 | 60 | 100 | 80 | 100 |
| Compound No. 3 | 80 | 100 | 35 | 100 | 100 | 100 |
| Compound No. 4 | 100 | 100 | 65 | 90 | 55 | 90 |
| Control compounds: | | | | | | |
| Compound A | 20 | 30 | 0 | 10 | 0 | 0 |
| Compound B | 0 | 0 | 0 | 0 | 0 | 0 |
| Compound C | 20 | 30 | 0 | 0 | 0 | 0 |
| Compound D | 25 | 45 | 0 | 30 | 0 | 0 |
| Compound E | 20 | 40 | 0 | 0 | 0 | 0 |
| Compound F | 0 | 0 | 0 | 0 | 0 | 0 |
| Compound G | 5 | 35 | 0 | 5 | 0 | 0 |
| Non-treated | 0 | 0 | 0 | 0 | 0 | 0 |

Test Example 2

Insecticidal effect against *Chilo suppressalis*

By the same procedure as in Example 9, the test compounds comprising the compounds of the present invention, i.e. Compound Nos. 1, 2, 3 and 4, and control compounds, i.e. Compounds A through G, were processed into wettable powder, respectively, and the aqueous solutions of 0.4 and 2 ppm in concentration were prepared therefrom by the same method as stated under (a) of Test Example 1, whereby 10 rice seedlings (the height of a plant of 2 cm) were dipped in each of the insecticide solutions for 30 minutes. The seedlings thus treated were placed in the respective glass containers (diameter of 2 cm and depth of 5 cm), into which 10 third-instar larvae of *Chilo suppressalis* were released. The containers were covered with aluminum foil and allowed to stand in a room (25° C.), and a number of dead larvae 4 days after the larvae were released was checked. The test was repeated twice, and the test results as expressed in terms of mortality (%) are shown in Table 2.

TABLE 2

| Test compound | Mortality, % Spraying concn. ppm | |
|---|---|---|
| | 0.4 | 2 |
| The compounds of the present invention: | | |
| Compound No. 1 | 80 | 100 |
| Compound No. 2 | 70 | 100 |
| Compound No. 3 | 40 | 80 |
| Compound No. 4 | 75 | 100 |
| Control compounds: | | |
| Compound A | 5 | 40 |
| Compound B | 0 | 0 |
| Compound C | 0 | 0 |
| Compound D | 10 | 45 |
| Compound E | 0 | 0 |
| Compound F | 0 | 0 |
| Compound G | 10 | 55 |
| Non-treated | 0 | 0 |

Test Example 3

Insecticidal effect against *Plutella xylostella*

By the same procedure as in Example 9, the test compounds comprising the compounds of the present invention, i.e., Compound Nos. 1, 2, 3 and 4, and control compounds, i.e. Compounds A through G, were processed into wettable powder, and the aqueous solutions of 50 ppm in concentration were prepared therefrom by the same method as stated under (a) of Test Example 1. 20 ml of each of the aqueous solutions was sprayed on seedlings of radish (25 days after germination) grown in pots in accordance with the same method as described under (a) of Test Example 1. 2 hours after the spraying, two true leaves were cut away and contained in their respective ice cream cups (diameter of 6 cm and depth of 4 cm), into which 10 second-instar larvae of *Plutella xylostella* were released. After the larvae were released, the above-mentioned cups were placed in a room (25° C.), and a number of dead larvae after 48 hours was checked. The test was repeated twice, and the test results as expressed in terms of mortality (%) are shown in Table 3.

TABLE 3

| Test compound | Mortality, % |
|---|---|
| The compounds of the present invention: | |
| Compound No. 1 | 100 |
| Compound No. 2 | 100 |
| Compound No. 3 | 95 |
| Compound No. 4 | 100 |
| Control compounds: | |
| Compound A | 20 |
| Compound B | 0 |
| Compound C | 10 |
| Compound D | 45 |
| Compound E | 40 |
| Compound F | 20 |
| Compound G | 50 |
| Non-treated | 0 |

What is claimed is:
1. A compound of the formula:

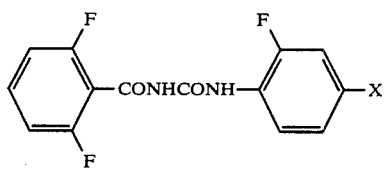

wherein X is a halogen.
2. A compound according to claim 1 wherein X is chlorine or bromine.
3. A compound according to claim 1 wherein X is chlorine.
4. A compound according to claim 1 wherein X is bromine.
5. A compound according to claim 1 wherein X is fluorine.
6. A compound according to claim 1 wherein X is iodine.
7. An insecticidal composition which comprises an effective amount of a compound of the formula:

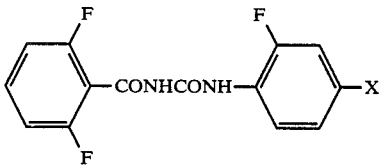

wherein X is a halogen, as an insecticidal ingredient; and a carrier thereof.
8. An insecticidal composition according to claim 7 wherein X is chlorine or bromine.
9. An insecticidal composition according to claim 7 wherein X is chlorine.
10. An insecticidal composition according to claim 7 wherein X is bromine.
11. An insecticidal composition according to claim 7 wherein X is fluorine.
12. An insecticidal composition according to claim 7 wherein X is iodine.
13. A method for killing insects which comprises contacting the insect with a compound of the formula:

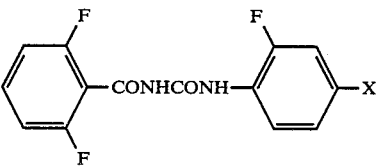

wherein X is a halogen.
14. A method for killing insects according to claim 13, wherein X is chlorine or bromine.
15. A method for killing insects according to claim 13, wherein X is chlorine.
16. A method for killing insects according to claim 13, wherein X is bromine.
17. A method for killing insects according to claim 13, wherein X is fluorine.
18. A method for killing insects according to claim 13, wherein X is iodine.

* * * * *